United States Patent [19]

Sakaigawa et al.

[11] Patent Number: 6,007,739

[45] Date of Patent: Dec. 28, 1999

[54] LIQUID CRYSTAL COMPOUND, LIQUID CRYSTAL COMPOSITION, AND LIQUID CRYSTAL DISPLAY DEVICE USING THE SAME

[75] Inventors: Akira Sakaigawa, Kawasaki; Aya Miyazaki, Tenri; Mitsuhiro Koden, Kashiwa; Kazuhiko Tsuchiya; Kenji Suzuki, both of Soka, all of Japan

[73] Assignees: Sharp Kabushiki Kaisha, Osaka; Kanto Kagaku Kabushiki Kaisha, Tokyo, both of Japan

[21] Appl. No.: 09/089,942

[22] Filed: Jun. 3, 1998

[30] Foreign Application Priority Data

Jun. 3, 1997 [JP] Japan ................................. 9-145642

[51] Int. Cl.$^6$ ..................... C09K 19/34; C07D 275/02; C07D 261/02; C07D 261/04; G02F 1/13

[52] U.S. Cl. .................... 252/299.61; 349/172; 349/188; 548/206; 548/214; 548/240; 548/247; 548/249

[58] Field of Search ........................ 252/299.61; 548/206, 548/214, 240, 247, 249; 349/188, 172

[56] References Cited

FOREIGN PATENT DOCUMENTS 60-054375 A  3/1985  Japan .

OTHER PUBLICATIONS

*Paris Liquid Crysal Conference*, p. 127, 1984.
"Mesogenic behaviour in some pyrazole and isoxazole derivatives", by J. Barbera et al. *Liquid Crystals* vol. 11, No. 6, pp. 887–897, 1992.
"Synthesis and thermotropic properties of new mesogenic pyrazole . . . " by C.G. Seguel et al., *Liquid Crystals* vol. 11, No. 6, pp. 899–903, 1992.
"Synthesis and Mesomorphic Properties of 3,5–bis–(p–n–Alkoxyphenyul) . . . " by J. Bartulin et al., *Mol. Cryst. Liq. Cryst* vol. 225 pp. 175–182, 1993.
"Ferroelectric Liquid Crystals" by R. B. Meyer et al., *Le Journal de Physique Letters* 36, pp. L69–L71, 1975.
"Submicrosecond bistable electro–optic switching in liquid crystals" by N. Clark et al. *Appl. Phys. Lett.* vol. 36, No. 11, pp. 899–901, 1980.
"A Multiplexed Ferroelectric LCD Using ac Field–Stabilized States" by J. Geary *SID 85 Digest* pp. 128–130, 1985.

(List continued on next page.)

*Primary Examiner*—Shean C. Wu
*Attorney, Agent, or Firm*—Birch, Stewart, Kolasch & Birch, LLP

[57] ABSTRACT

A liquid crystal compound of the present invention is represented by the following general Formula I:

$$R_1 \text{-phenyl}(X_1, X_2) \text{-} Y \text{-phenyl}(X_3, X_4) \text{-} R_2 \quad (I)$$

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

(II) isoxazole ring (N—O)

(III) isothiazole ring (N—S)

15 Claims, 8 Drawing Sheets

OTHER PUBLICATIONS

"Color Digital Ferroelectric LCDs for Laptop Applications" by P. Ross et al. *SID 92 Digest* pp. 217–220, 1992.

"The 'Joers/Alvey' Ferroelectric Multiplexing Scheme" by P.W.H. Surguy et al. *Ferroelectrics* vol. 122, pp. 63–79, 1991.

"High Resolution, Large Area FLC Display with High Graphic Performance" by J. Kanbe et al. *Ferroelectrics* vol. 114, pp. 3–26, 1991.

*Mol. Cryst. Liq. Cryst.*, vol. 22 (1992), pp. 67–75, "Synthesis and Mesomorphic Properties of the 3,5–Bis–alkoxyphenyl–Pyrazoles and–Isoxazoles".

CAPLUS 1992: 561422. 1992.

LIQUID CRYSTAL COMPOUND, LIQUID CRYSTAL COMPOSITION, AND LIQUID CRYSTAL DISPLAY DEVICE USING THE SAME

BACKGROUND OF THE INVENTION

1. Field of the Invention

The present invention relates to a liquid crystal display device used for a display of a clock, a calculator, a word processor, a small TV set, etc., and a liquid crystal compound and a liquid crystal composition (in particular, a ferroelectric liquid crystal composition) preferably used for the liquid crystal display device.

2. Description of the Related Art

At present, most of the above-mentioned liquid crystal display device s use a TN (twisted nematic) display system. TN liquid crystal display devices, which utilize a nematic liquid crystal composition, are roughly classified into two groups.

One group includes liquid crystal display devices which utilize an active matrix system in which a switching element, e.g., TFT (thin film transistor), is provided at each pixel. The active matrix system realizes a display quality comparable to that of a CRT (cathode ray tube). However, due to the complicated structure, it is costly to produce a large active matrix liquid crystal display device.

The other group includes liquid crystal display devices which utilize an STN (super twisted nematic) system. The STN system realizes an improved contrast and viewing angle characteristic, compared with those of a conventional simple matrix system. However, the STN system is not suitable for displaying animations because of its slow response speed. Furthermore, the STN system has the disadvantage of a lower display quality than that of the active matrix system using TFTs. On the other hand, the STN system can be produced at low cost. Considering a display quality and a production cost, the active matrix system and the STN system respectively have both advantages and disadvantages.

An example of a display system overcoming the above-mentioned problems includes a liquid crystal display system using ferroelectric liquid crystal (FLC) which is smectic liquid crystal exhibiting spontaneous polarization (R. B. Meyer et al., Journal de physique, 36L–69 (1975)). When the ferroelectric liquid crystal is placed between a pair of substrates (cell) opposing each other with a gap of several μm therebetween, the helical structure of the liquid crystal is eliminated, so that bistable switching having a memory effect can be realized. Such ferroelectric liquid crystal is called surface stabilized ferroelectric liquid crystal (SSFLC). Currently, ferroelectric liquid crystal refers only to SSFLC. SSFLC was proposed by N. A. Clark, S. T. Lagerwall, Appl. Phys. Lett., 36, 899 (1980).

The SSFLC system has a high response and a memory property 100 to 1000 times as high as those of the conventional liquid crystal display device using nematic liquid crystal, and furthermore, has a wide viewing angle characteristic. These properties suggest the usefulness of SSFLC for a large capacity display.

However, as the study proceeds, problems of SSFLC which should be overcome are becoming apparent. Among them, it is the first objective to obtain a stable memory property. The reason why it is difficult to obtain a stable memory property in SSFLC lies in nonuniform smectic layer structure (e.g., twisted alignment, a chevron structure, etc.), and the generation of an inner reverse electric field which is considered to be caused by the excessively high spontaneous polarization.

As one means for obtaining a stable memory property, an AC stabilizing effect using a ferroelectric liquid crystal composition having a negative dielectric anisotropy (hereinafter, referred to as "$\Delta\epsilon$") has been proposed (Paris Liquid Crystal Conference, p. 217 (1984)). Hereinafter, the AC stabilizing effect will be described.

Liquid crystal molecules having a negative $\Delta\epsilon$ have the property that they are aligned parallel to substrates (i.e. molecule long axes are aligned vertically to the direction of an electric field) while an electric field is being applied in a direction vertical to electrodes provided on the substrates in a cell subjected to a homogeneous alignment treatment. In the case where a low frequency electric field is applied, spontaneous polarization of the liquid crystal molecules can follow the inversion of the electric field. Therefore, the liquid crystal molecules move to another stable state along with the inversion of direction of the electric field and become parallel to the substrates due to the effect of $\Delta\epsilon$. In contrast, in the case where a high frequency electric field is applied, spontaneous polarization of the liquid crystal molecules does not follow the inversion of the electric field. Therefore, only $\Delta\epsilon$ exerts its effect, and the liquid crystal molecules do not move while the direction of the electric field is inverted. Thus, the liquid crystal molecules remain parallel to the substrates. This is a mechanism of obtaining a memory property utilizing the AC stabilizing effect, which enables a high contrast to be obtained. An example of the AC stabilizing effect has already been reported in SID'85 Digest, p. 128 (1985).

Regarding a method for utilizing a liquid crystal material having a negative $\Delta\epsilon$, a $\tau$-$V_{min}$ driving method has been proposed by Surguy et al. (P.W.H. Ferroelectrics, 122, 63 (1991)). This is a promising method for realizing a high contrast, and P. W. Ross, SID'92, 217 (1992) discloses a ferroelectric liquid crystal display using this method. Hereinafter, the $\tau$-$V_{min}$ driving method will be described.

In the case of ferroelectric liquid crystal not having a negative $\Delta\epsilon$, a pulse width required for memory monotonously decreases with the increase in a driving voltage (V). On the other hand, in the case of ferroelectric liquid crystal having a negative $\Delta\epsilon$, a voltage (V)-memory pulse width ($\tau$) characteristic has a local minimum ($\tau$-$V_{min}$), as shown in FIG. 9. Surguy et al. has reported a JOERS/Alvey driving method using this characteristic. The principle of this driving method is as follows: as shown in FIG. 10, assuming that $V_s$ is a scanning voltage and $V_d$ is a data voltage, a memory state of a ferroelectric liquid crystal device is switched when a voltage $|V_s-V_d|$ is applied, and the memory state is not switched when a voltage $|V_s-V_d|$ which is higher than the voltage $|V_s-V_d|$, or a voltage $|V_d|$ which is lower than the $|V_s-V_d|$, is applied.

As described above, the ferroelectric liquid crystal material having a negative $\Delta\epsilon$ can utilize the AC stabilizing effect and the $\tau$-$V_{min}$ driving method. Therefore, there may be a possibility that the ferroelectric liquid crystal material having a negative $\Delta\epsilon$ can be used to realize a ferroelectric liquid crystal display device with a high contrast and a high-speed switching.

In the case where the above-mentioned ferroelectric liquid crystal material is actually used for a liquid crystal display device, a number of characteristics are required. However, at present, it is difficult to satisfy all the requirements by a single compound. Thus, generally, optimization of characteristics is conducted by mixing various compounds. For example, in the case of a ferroelectric liquid crystal material having a negative Δε which has a low viscosity and a high-speed response, it requires a high driving voltage. The driving voltage can be decreased by mixing a material having a negative Δε with a large absolute value therewith.

Hithertofore, some liquid crystal compounds have been reported. For example, Japanese Laid-open Publication No. 60-54375 discloses the following compound:

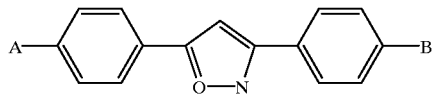

(i)

wherein either one of A and B is an alkyl group or an alkoxy group having 1 to 15 carbon atoms, and the other is a chlorine atom or a fluorine atom.

Furthermore, J. Barbera et al., LIQUID CRYSTALS, Vol. 11, No. 6 (1992) 887–897., C. G. Seguel et al., LIQUID CRYSTALS, Vol. 11, No. 6 (1992) 899–903, and J. Bartulin et al., Mol. Cryst. Liq. Cryst., Vol. 225 (1993) 175–182 discloses the following compound:

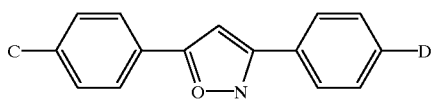

(ii)

wherein C and D are alkoxy groups.

The compound represented by the above Formula (i) is nematic liquid crystal having a positive Δε and does not exhibit a smectic phase. Thus, the compound (i) is not suitable as a ferroelectric liquid crystal material. On the other hand, the compound represented by the above Formula (ii) exhibits a smectic phase and is suitable as a ferroelectric liquid crystal material. However, the compound (ii) also has the disadvantage that it has a high viscosity due to two alkoxy groups on C and D.

Irrespective of whether or not the above-mentioned τ-$V_{min}$ driving method is used, in order to realize a high switching in ferroelectric liquid crystal, a material having large spontaneous polarization and a low viscosity is generally required. This is represented by the following Formula:

$$\tau \propto \eta / P_s$$

wherein τ is a response time or a pulse width required for memory; η is a viscosity; and $P_s$ is spontaneous polarization.

However, according to the τ-$V_{min}$ driving method, the following relationship holds between a voltage $V_{min}$ and $P_s$ where τ becomes a local minimum $\tau_{min}$:

$$V_{min} = P_s \cdot d / (\sqrt{3} \cdot \varepsilon_o \cdot \Delta\varepsilon \cdot \sin^2\theta)$$

wherein d is a cell thickness; $\varepsilon_0$ is a dielectric constant in a vacuum; Δε is a dielectric anisotropy; and θ is a tilt angle. As is understood from this formula, when the spontaneous polarization $P_s$ is increased in order to realize a high-speed switching, $V_{min}$ is also increased. This results in a high driving voltage and an increase in power consumption.

Accordingly, in order to realize high-speed driving while retaining $V_{min}$ at a low level, a ferroelectric liquid crystal material having a negative Δε with a large absolute value and a low viscosity is required. In order to obtain a stable memory property using the above-mentioned AC stabilizing effect, a ferroelectric liquid crystal material having a negative Δε with a large absolute value is also required.

However, the compound (i) is nematic liquid crystal having a positive Δε, so that it cannot be used as a ferroelectric liquid crystal material having a negative Δε. Furthermore, the compound (ii) has a high viscosity (i.e., is likely to have a high phase transition temperature), so that a driving voltage cannot be decreased.

SUMMARY OF THE INVENTION

A liquid crystal compound of the present invention is represented by the following general formula I:

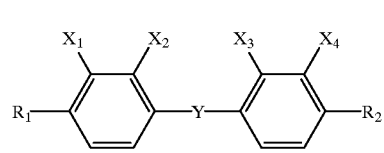

(I)

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

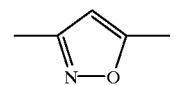

(II)

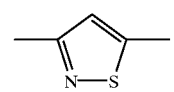

(III)

In one embodiment of the present invention, —Y— in the general Formula (I) is a group represented by the Formula (II).

In another embodiment of the present invention, the above-mentioned liquid crystal compound has a negative dielectric anisotropy Δε.

A liquid crystal composition of the present invention includes at least one kind of liquid crystal compound represented by the following general Formula (I):

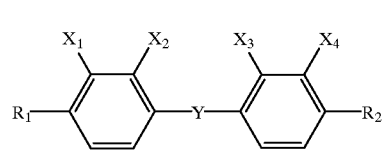

(I)

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

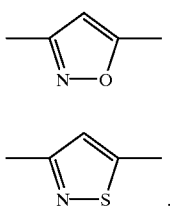

(II)

(III)

In one embodiment of the present invention, the above-mentioned liquid crystal composition has a negative dielectric anisotropy $\Delta\epsilon$.

In another embodiment of the present invention, the above-mentioned liquid crystal composition has a phase series exhibiting isotropic liquid, a nematic phase, a smectic A phase, and a smectic C phase in a decreasing order of temperature.

In another embodiment of the present invention, the above-mentioned liquid crystal composition has ferroelectricity.

In another embodiment of the present invention, the above-mentioned liquid crystal composition further includes at least one kind of optically active compound.

A liquid crystal display device of the present invention includes a pair of substrates opposing each other and a liquid crystal layer provided between the substrates, the liquid crystal layer containing a ferroelectric liquid crystal composition containing at least one kind of liquid crystal compound represented by the following general Formula (I):

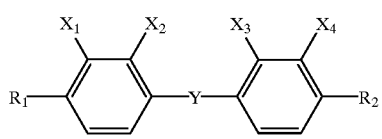

(I)

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

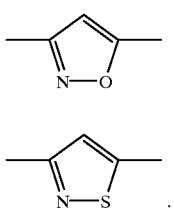

(II)

(III)

In one embodiment of the present invention, the liquid crystal layer has an identical pretilt angle at an interface between the liquid crystal layer and one of the pair of substrates with a pretilt angle at an interface between the liquid crystal layer and the other of the pair of substrates, and has a chevron layer structure, wherein a bending direction of the chevron layer structure is identical with a direction of the pretilt angle.

In another embodiment of the present invention, the ferroelectric liquid crystal composition has a negative dielectric anisotropy $\Delta\epsilon$ and a local minimum value in a voltage-memory pulse width characteristic.

In another embodiment of the present invention, the pretilt angle is in a range of 1° to 15°.

Hereinafter, the function of the present invention will be described.

According to the present invention, the novel liquid crystal compound having the structure represented by the above-mentioned Formula (I) is obtained. In the liquid crystal compound of the present invention, $R_1$ and $R_2$ are alkyl groups or alkoxy groups, at least one of $R_1$ and $R_2$ is an alkyl group, and a fluorine atom may be present at a particular position of a benzene ring. Therefore, the liquid crystal compound of the present invention exhibits a liquid crystal phase in a wider range of temperatures. Furthermore, the liquid crystal compound of the present invention has a lower phase transition temperature, a lower viscosity, and a lower driving voltage, compared with those of the compound in which $R_1$ and $R_2$ are both alkoxy groups as represented by the above Formula (V).

In a preferred embodiment of the present invention, since at least one of $X_1$, $X_2$, $X_3$, and $X_4$ is a fluorine atom, the liquid crystal compound of the present invention has a lower phase transition temperature and a lower viscosity, and a negative $\Delta\epsilon$ with a larger absolute value, compared with the compound in which $X_1$, $X_2$, $X_3$, and $X_4$ are all hydrogen atoms.

In another preferred embodiment of the present invention, the liquid crystal compound of the present invention has a negative $\Delta\epsilon$, so that a liquid crystal composition having a negative $\Delta\epsilon$ can be obtained by mixing at least one kind of the compound of the present invention with another material (which may be any suitable liquid crystal material having a positive $\Delta\epsilon$). Thus, in the case of using the liquid crystal composition (in particular, a ferroelectric liquid crystal composition) of the present invention having a negative $\Delta\epsilon$ in a liquid crystal display device, a stable memory property can be obtained due to the AC stabilizing effect, and a high contrast can be realized. Furthermore, the liquid crystal composition of the present invention exhibits a voltage-memory pulse width characteristic having a local minimum value ($\tau$-$V_{min}$), so that a stable high-speed switching is made possible by the $\tau$-$V_{min}$ driving method. Furthermore, the liquid crystal composition of the present invention has a negative $\Delta\epsilon$ with a large absolute value and a low viscosity, so that high-speed driving is made possible at a low voltage by the $\tau$-$V_{min}$ driving method.

In another preferred embodiment of the present invention, the liquid crystal display device of the present invention has a C2 alignment in which the bending direction of a chevron layer structure is identical with the direction of a pretilt angle, so that a lower driving voltage, a higher response speed, and an improved extinction property can be obtained.

Thus, the invention described herein makes possible the advantages of (1) providing a novel liquid crystal compound which can be preferably used for a liquid crystal display device (which has a negative $\Delta\epsilon$ with a large absolute value and a low viscosity) and a liquid crystal composition (in particular, a ferroelectric liquid crystal composition) containing the same; and (2) providing a liquid crystal display device using such a liquid crystal compound and the liquid crystal composition containing the compound, in which a stable memory property is obtained and which can be driven at a high speed at a low voltage.

These and other advantages of the present invention will become apparent to those skilled in the art upon reading and understanding the following detailed description with reference to the accompanying figures.

DESCRIPTION OF THE PREFERRED EMBODIMENTS

Hereinafter, the present invention will be described by way of illustrative embodiments. The present invention is not limited by the embodiments.

A compound of the present invention is represented by the following general Formula (I):

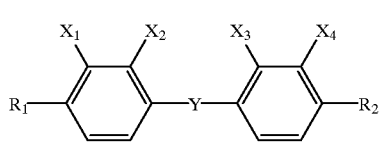

(I)

wherein $R_1$ and $R_2$ are independently linear or branched alkyl groups or alkoxy groups having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

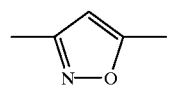

(II)

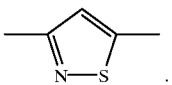

(III)

$R_1$ and $R_2$ independently have preferably 5 to 14 carbon atoms, more preferably 5 to 10 carbon atoms. $R_1$ and $R_2$ may be linear or branched, and they are preferably linear.

Furthermore, preferably, at least one of $X_1$, $X_2$, $X_3$, and $X_4$ is a fluorine atom, and more preferably, at least two of them are fluorine atoms.

Preferably, —Y— in the above-mentioned general Formula (I) is a group represented by the above-mentioned Formula (II).

Preferably, a liquid crystal compound of the present invention has a negative Δε.

An example of a synthesis route of the liquid crystal compound of the present invention will be described with reference to FIG. 1.

(Synthesis of isoxazole represented by the following general Formula (1a))

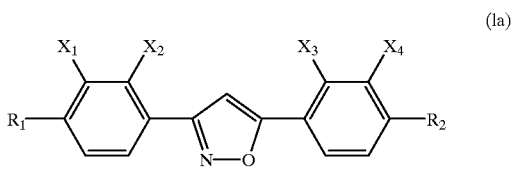

(1a)

wherein $R_1$, $R_2$, $X_1$, $X_2$, $X_3$, and $X_4$ are the same as described above.

(Synthesis route 1)

Figure 1:
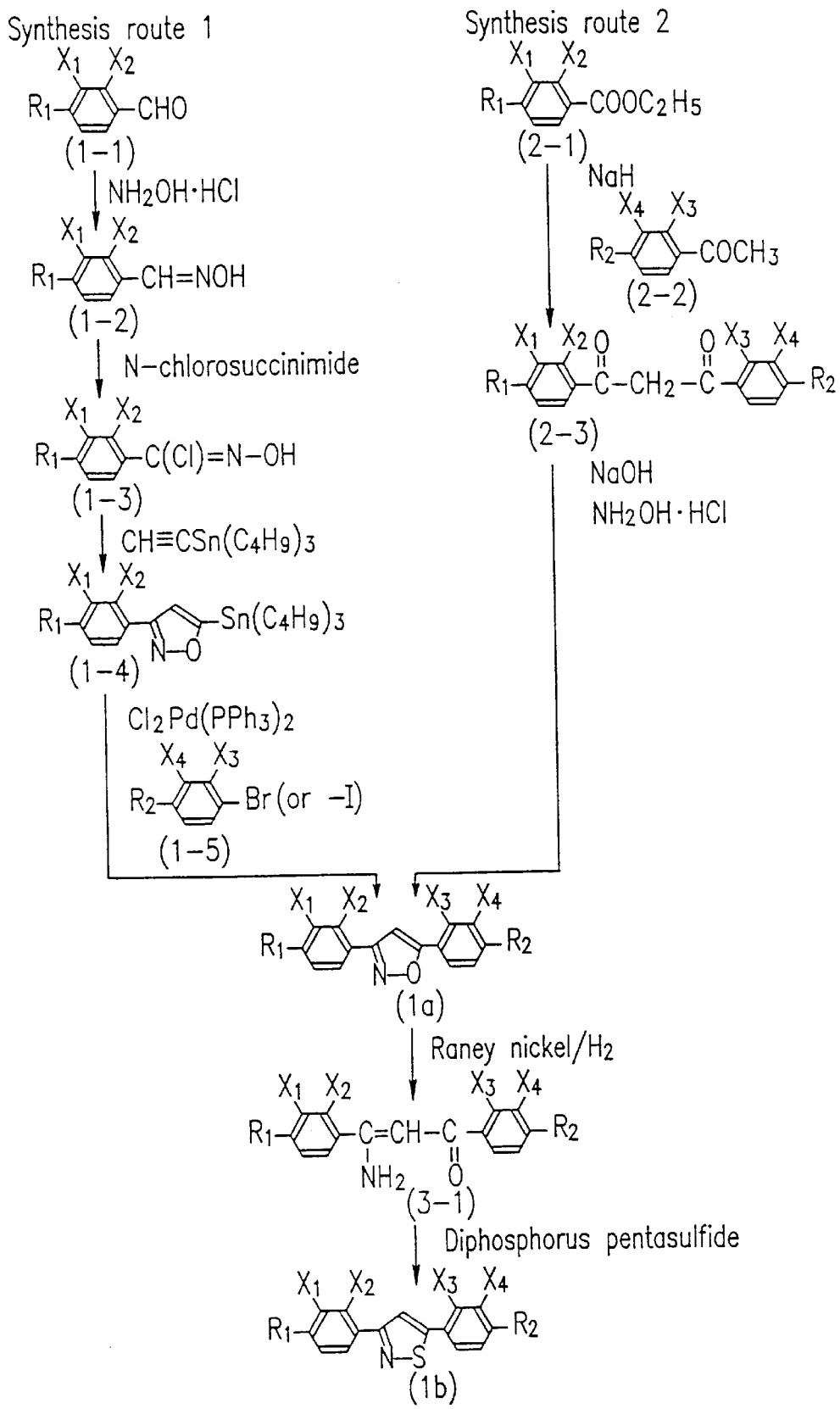
FIG. 1 is a reaction scheme showing examples of synthesis routes of a liquid crystal compound in one embodiment of the present invention.

A compound (1-1) shown in FIG. 1 is reacted with hydroxylamine hydrochloride in the presence of an alkali to obtain a compound (1-2). Then, the compound (1-2) is chlorinated with N-chlorosuccinimide to obtain a compound (1-3).

Next, the compound (1-3) is reacted with commercially available ethynyltributyltin in the presence of triethylamine to obtain a compound (1-4). Thereafter, the compound (1-4) is coupled with a compound (1-5), using dichlorobis (triphenylphosphine)palladium (II) as a catalyst to obtain isoxazole represented by the general Formula (1a).

(Synthesis route 2)

A compound (2-1) shown in FIG. 1 is reacted with a compound (2-2) in the presence of an alkali to obtain a compound (2-3). Then, the compound (2-3) is subjected to a ring closure reaction with hydroxylamine hydrochloride in the presence of an alkali to obtain isoxazole represented by the general Formula (1a).

(Synthesis of isothiazole represented by the following general Formula (1b))

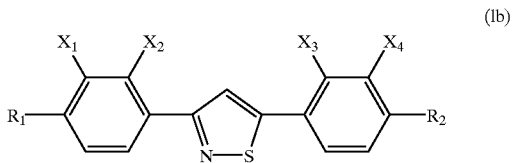

(1b)

wherein $R_1$, $R_2$, $X_1$, $X_2$, $X_3$, and $X_4$ are the same as described above.

An isoxazole ring of the compound (1a) obtained through the Synthesis route 1 or the Synthesis route 2 is subjected to a ring-opening reaction, using Raney nickel and hydrogen to obtain a compound (3-1). The compound (3-1) is reacted with diphosphorus pentasulfide to obtain isothiazole represented by the general Formula (1b).

The liquid crystal compound of the present invention thus obtained has a negative Δε and a lower viscosity than that of the conventional compound represented by the above-mentioned Formula (ii).

In the case where one of $R_1$ and $R_2$ is an alkoxy group in the above-mentioned Formulae (1a) and (1b), the liquid crystal compound exhibits a liquid crystal phase in a wider range of temperatures, compared with the case where both of $R_1$ and $R_2$ are alkyl groups.

In the case where at least one (preferably, at least two) of $X_1$, $X_2$, $X_3$, and $X_4$ is a fluorine atom, the liquid crystal compound has a lower phase transition temperature and a negative Δε with a larger absolute value, compared with the case where $X_1$, $X_2$, $X_3$, and $X_4$ are all hydrogen atoms.

Next, a liquid crystal composition of the present invention will be described.

The liquid crystal composition of the present invention contains at least one kind of the liquid crystal compound of the present invention, and preferably has a negative Δε. The liquid crystal composition of the present invention can be adjusted by mixing the liquid crystal compound of the present invention with any appropriate liquid crystal compound and/or any appropriate liquid crystal composition. In this case, the liquid crystal compound and the liquid crystal composition to be mixed may not have a negative Δε. This is because the resultant liquid crystal composition can have a negative Δε by containing the liquid crystal compound of the present invention in an appropriate proportion.

The liquid crystal compound of the present invention may be contained in any proportion in the liquid crystal composition of the present invention, as long as the objective of the present invention of providing the resultant liquid crystal composition with a negative Δε with a large absolute value is satisfied. Practically, the liquid crystal compound of the present invention can be contained in the liquid crystal composition in a proportion of, for example, 1% to 90%, preferably 5 to 50%, more preferably 5 to 30%. The liquid crystal compound of the present invention itself exhibits a liquid crystal phase, so that it can be contained in the liquid crystal composition in a proportion of 90%.

Preferably, the liquid crystal composition of the present invention has ferroelectricity. Furthermore, the liquid crystal composition of the present invention can be adjusted so as to have a phase series exhibiting isotropic liquid, a nematic phase, a smectic A phase, and a smectic C phase in a decreasing order of temperature, in terms of the alignment in the ferroelectric liquid crystal composition.

The ferroelectric liquid crystal composition of the present invention may further contain at least one kind of optically active material. Examples of the optically active material include a compound represented by the following Formula (IV) or (V) or a mixture thereof.

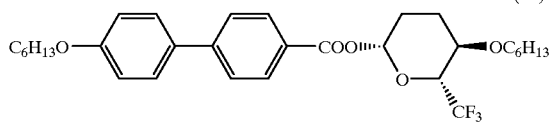

(IV)

-continued

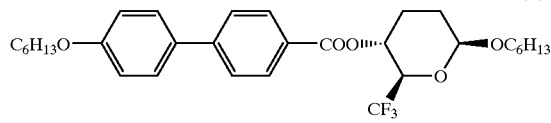

(V)

Next, a liquid crystal display device of the present invention will be described with reference to the drawings.

Figure 2:
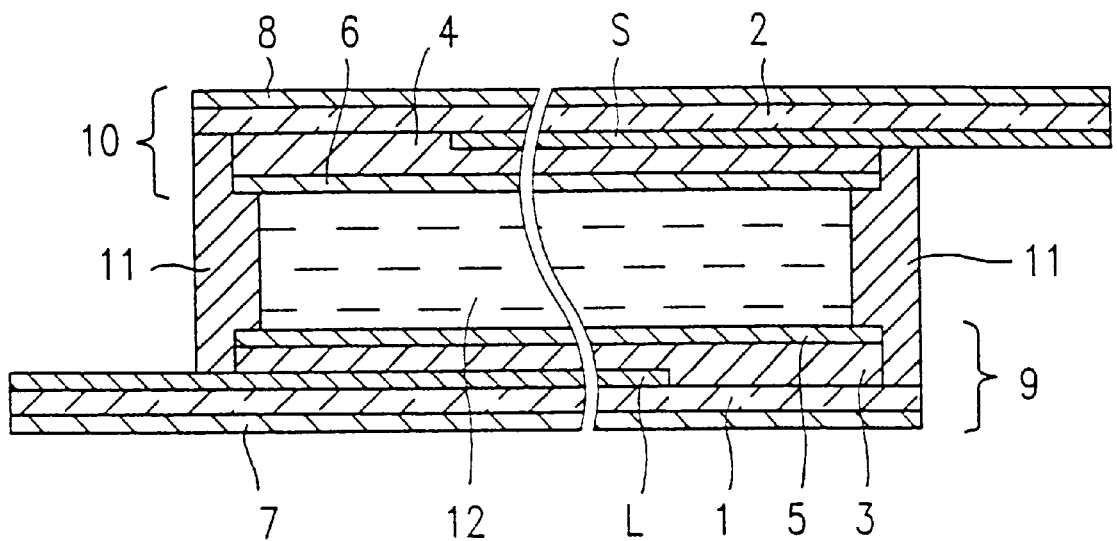
FIG. 2 is a cross-sectional view showing a basic structure of a liquid crystal display device in one embodiment of the present invention.

FIG. 2 is a cross-sectional view showing a basic structure of the liquid crystal display device of the present invention. The liquid crystal display device has a substrate 9 having electrodes S made of a conductive film on an insulating substrate 1 and a substrate 10 having electrodes L made of a conductive film on an insulating substrate 2. The substrates 9 and 10 oppose each other. A liquid crystal layer 12 containing a ferroelectric liquid crystal composition of the present invention is provided between the substrates 9 and 10. An optical axis of each portion (pixel) of the liquid crystal layer 12 is switched by selectively applying a voltage to the electrodes S and L on each of the substrates 9 and 10. For the purpose of identifying the switching of the optic axis, polarizing plates 7 and 8 are provided on opposite sides of the substrates 9 and 10 with respect to the liquid crystal layer 12. In FIG. 2, reference numerals 3 and 4 denote insulating films, 5 and 6 denote alignment films, and 11 denotes a sealant.

The liquid crystal display device can be produced, for example, as follows.

As the above-mentioned insulating substrates 1 and 2, substrates with high light transparency (generally, glass substrates) are used. Transparent conductive films made of $InO_3$, $Sno_2$, or ITO (indium tin oxide), etc. are formed on the insulating substrates 1 and 2 by a CVD (chemical vapor deposition) method or sputtering, whereby the electrodes S and L with a predetermined pattern are formed. The thickness of the transparent conductive film is preferably in a range of 50 nm to 200 nm.

Then, the insulating films 3 and 4 are formed to a thickness of about 20 nm to about 200 nm on the electrodes S and L. As the insulating films 3 and 4, inorganic thin films made of $SiO_2$, $SiN_x$, $Al_2O$, $Ta_2O_5$, etc. or organic thin films made of polyimide, photoresist resin, polymer liquid crystal, etc. can be used. In the case where the insulating films 3 and 4 are inorganic thin films, they can be formed by vapor deposition, sputtering, a CVD method, solution coating, etc. In the case where the insulating films 3 and 4 are organic thin films, they are formed as follows: a solution in which an organic material is dissolved or its precursor solution is coated by spin coating, dip coating, screen printing, or roll coating, and the solution thus coated is cured under predetermined curing conditions (heating, light irradiation, etc.). The insulating films 3 and 4 can be omitted.

Then, the alignment films 5 and 6 with a thickness of 10 nm to 100 nm are formed on the insulating films 3 and 4. In the case where the insulating films 3 and 4 are omitted, the alignment films 5 and 6 are formed directly on the electrodes S and L. The alignment films 5 and 6 may be inorganic alignment films or organic alignment films. As the inorganic alignment film, silicon oxide or the like can be used. As the method for forming the alignment film, known methods such as an oblique evaporation method or a rotation evaporation method can be used. As the organic alignment film, nylon, polyvinyl alcohol, polyimide or the like can be used. Generally, the alignment films are subjected to rubbing. In the case where polymer liquid crystal, an LB film, or the like is used as the alignment films 5 and 6, the alignment films 5 and 6 can be aligned magnetically or by a spacer edge method. Furthermore, a film of $SiO_2$, $SiN_x$, or the like may be formed by an evaporation method, sputtering, or a CVD method, followed by rubbing, if necessary. The alignment films 5 and 6 are preferably aligned in such a manner that liquid crystal molecules have the same pretilt angle at the interface with one of a pair of substrates and at the interface with the other of a pair of substrates.

Thereafter, the substrates 9 and 10 are attached to each other with the sealant 11 interposed therebetween, and a liquid crystal composition is injected between the substrates 9 and 10, whereby a liquid crystal display device is obtained.

Figure 3:
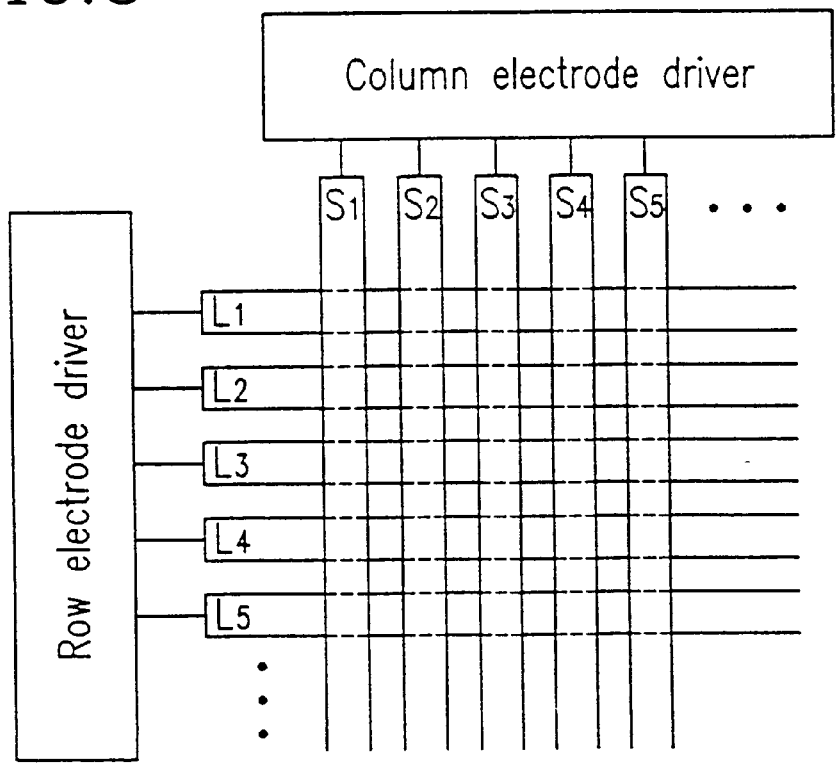
FIG. 3 is a schematic plan view showing a structure of electrodes and electrode drivers in the liquid crystal display device shown in FIG. 2.

FIG. 2 shows a structure of a liquid crystal display device having one pixel. However, the liquid crystal display device of the present invention is applicable to a display device with a large capacity matrix. In this case, as shown in a schematic plan view of FIG. 3, electrode lines S1, S2, S3, . . . in a column direction and electrode lines L1, L2, L3, . . . in a row direction are provided on the substrates 9 and 10 in a matrix.

A method for providing the liquid crystal layer 12 between a pair of substrates is not particularly limited. For example, the peripheral portion of the substrates 9 and 10 are attached with the sealant 11, and thereafter, a liquid crystal composition is injected between the substrates 9 and 10 by a vacuum injection method or the like. Alternatively, a liquid crystal composition is coated onto one of the substrates 9 and 10 by a printing method or the like, and thereafter, the peripheral portion of the substrates 9 and 10 are attached with the sealant 11. Spacers may be dispersed between the substrates 9 and 10 so as to keep a uniform thickness of the liquid crystal layer 12. The diameter of the spacers is 1 μm to 30 μm, preferably 1 μm to 5 μm.

Hereinafter, an alignment state of the liquid crystal display device thus produced will be described.

Figure 4:
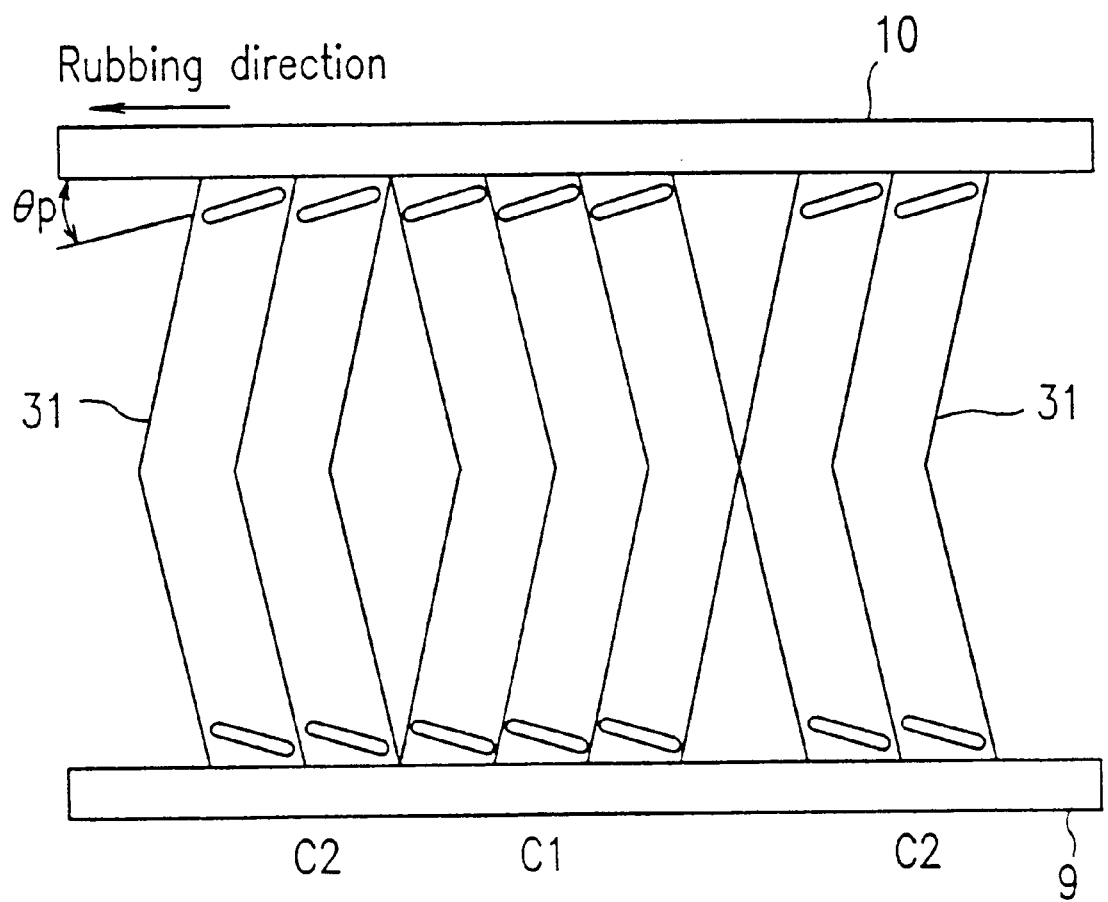
FIG. 4 is a schematic view illustrating a smectic phase forming a chevron structure in the liquid crystal display device shown in FIG. 2.
Figure 5:
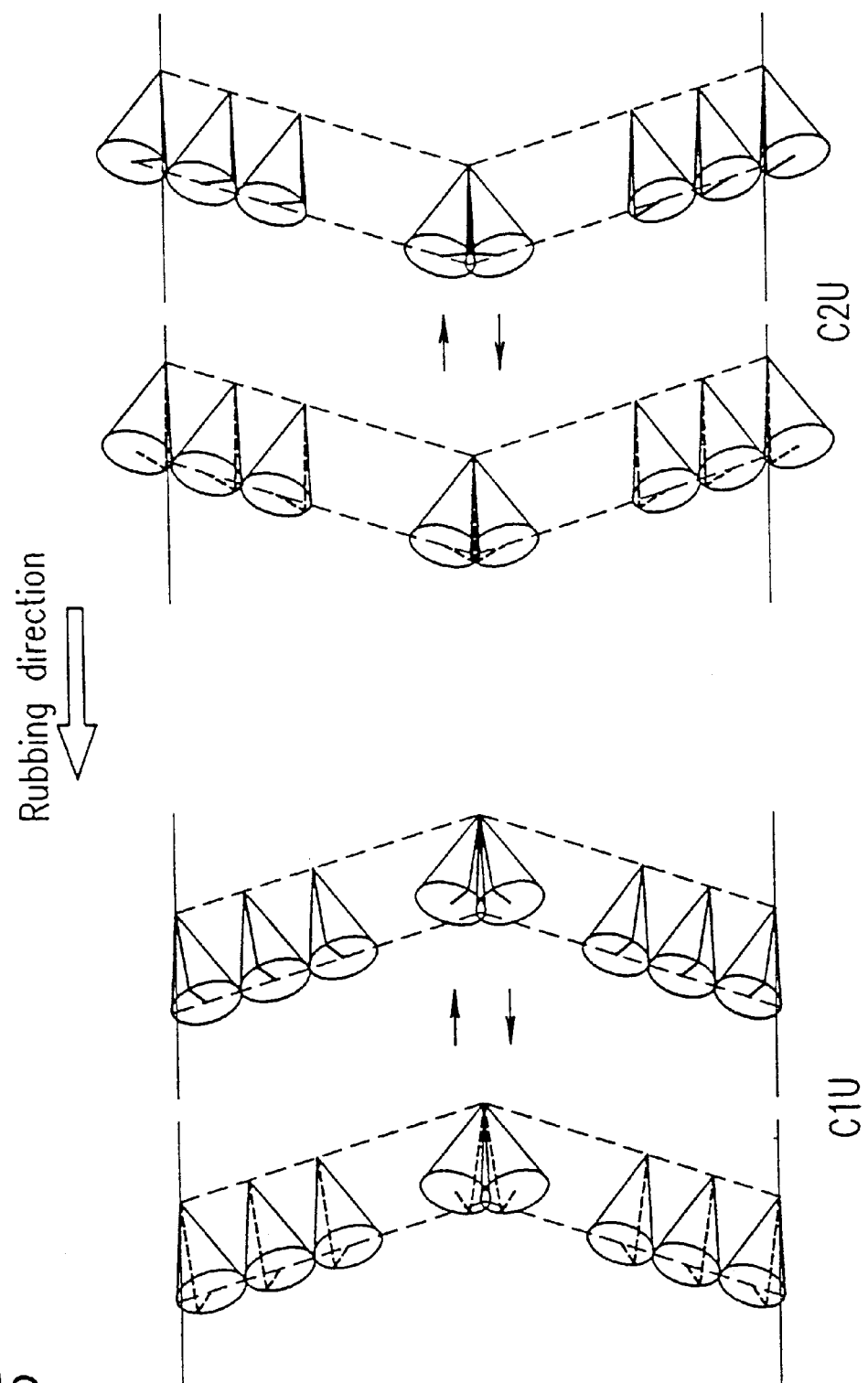
FIG. 5 is a schematic view illustrating alignment states of liquid crystal molecules in the smectic phase shown in FIG. 4.

In SSFLC, the liquid crystal layer 31 has a "<" or ">" shaped bending layer structure (i.e., a chevron structure: liquid crystal molecules are aligned in the shape of "<" or ">"), as shown in FIG. 4 or 5. It has been reported in J. Kanbe et al., Ferroelectrics, 114, 3 (1991) that in the chevron layer structure, there are a C2 alignment in which the bending direction of the chevron layer structure is identical with a rubbing direction of the substrates (i.e., the direction of a pretilt angle of liquid crystal molecules) and a C1 alignment in which the bending direction of the chevron layer structure is opposite to the rubbing direction of the substrates, and these two kinds of alignment states can be present in a single device. These two kinds of alignment states have different driving characteristics, and defects caused at the interface results in a decrease in contrast. Thus, as shown in FIG. 5, it is desirable that either of a C1U state in which the entire device becomes the C1 alignment state and a C2U in which the entire device becomes the C2 alignment state is obtained. Particularly, in terms of a driving voltage, a response speed, an extinction property, etc., the C2 alignment state in which the bending direction in the chevron layer structure is identical with the direction of a pretilt angle is desirable. An example of a technique of prescribing the entire device with the C2 alignment is disclosed in, for example, Japanese Laid-open Publication No. 8-101370. When an alignment film made of polyimide is subjected to a uniaxial alignment treatment by rubbing, a pretilt angle $\theta_p$ is formed. In the case where the pretilt angle $\theta_p$ is too small, the difference in free energy between the C1 alignment and the C2 alignment becomes small, making it difficult to obtain purely the C2 alignment in the entire device. In the case where the pretilt angle $\theta_p$ is too large, the C1 alignment becomes unlikely to shift to the C2 alignment. As a result, only the C1 alignment becomes stable during a temperature cooling process. Thus, the pretilt angle of the alignment film is desirably 1° to 15°, more desirably 1° to 10°.

In the liquid crystal display device, preferably, the ferroelectric liquid crystal composition has a negative $\Delta\epsilon$ and a local minimum value in a voltage-memory pulse width characteristic.

Hereinafter, the present invention will be described in more detail by way of illustrative examples.

In Examples 1 through 5, the liquid crystal compound of the present invention will be exemplified.

The abbreviations in the following examples and Tables are as follows:

TLC: thin layer chromatography
GC: gas chromatography
HPLC: high performance liquid chromatography
IR: infrared absorption spectrum
C,C': crystal
$S_x$: indistinguishable smectic phase
$S_c$: smectic C phase
$S_A$: smectic A phase
Ne: nematic phase
I: isotropic liquid

EXAMPLE 1

In Example 1, 3-(4-n-heptylphenyl)-5-(4-n-octylphenyl) isoxazole represented by the following Formula was synthesized.

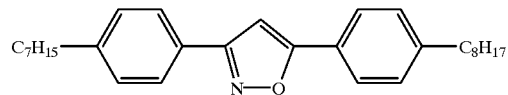

(a) Synthesis of 4-n-heptylbenzaldehydeoxime

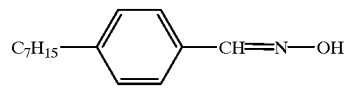

To a solution containing 40 g of 4-n-heptylbenzaldehyde and 200 ml of methanol, a solution containing 12.0 g of sodium carbonate and 50 ml of water and 17 g of hydroxylamine hydrochloride was added. The mixture was refluxed with stirring for 9 hours.

The reaction solution was poured into water, and an organic layer was extracted with ether. The ether layer was washed with water, and the resultant solution was dried with $Na_2SO_4$. Thereafter, the solvent was distilled off. The residue was recrystallized with hexane to obtain 4-n-heptylbenzaldehydeoxime (yield 37.9 g; Mass 219 (M+)).

(b) Synthesis of 4-n-heptylbenzohydroxyiminoyl chloride

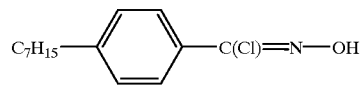

To a solution containing 7 g of 4-n-heptylbenzaldehydeoxime obtained in (a) and 30 ml of dimethylformamide, 4.27 g of N-chlorosuccinimide was added while the reaction temperature was kept in the vicinity of about 35° C. Thereafter, the reaction solution was stirred at room temperature for 2 days.

The reaction solution was poured into water, and an organic layer was extracted with ether. The ether layer was washed with water, and the resultant solution was dried with $Na_2SO_4$. Thereafter, the solvent was distilled off to obtain crude 4-n-heptylbenzohydroxyiminoyl chloride (yield 8.67 g; Mass 253 (M+)).

(C) Synthesis of 3-(4-n-heptylphenyl)-5-(tributyltin) isoxazole

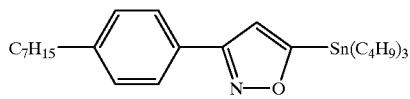

A solution containing 8.67 g of 4-n-heptylbenzohydroxyiminoyl chloride obtained in (b), 6.71 g of ethynyltributyltin, and 60 ml of benzene was cooled to 5° C. or less in an atmosphere of argon. Then, a solution containing 3.45 g of triethylamine and 10 ml of benzene was dropped onto the cooled solution, followed by stirring the resultant solution at the same temperature for one hour. Then, the solution was returned to room temperature and stirred overnight.

Triethylamine hydrochloride was filtered from the reaction solution. The filtrate obtained was poured into diluted hydrochloric acid, and an organic layer was extracted with benzene. The benzene layer was washed with water, and the resultant solution was dried with $Na_2SO_4$. Thereafter, the solvent was distilled off. The residue was purified by silica gel column chromatography using a mixed solvent of hexane-toluene (2:1) as an eluent to obtain 3-(4-n-heptylphenyl)-5-(tributyltin)isoxazole (yield 10.3 g; Mass 553 (M+) 476, 420, 362, 242).

(d) Synthesis of 3-(4-n-heptylphenyl)-5-(4-n-octylphenyl) isoxazole

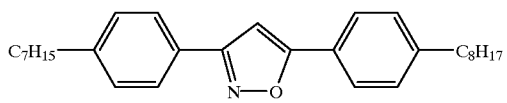

A mixture containing 0.24 g of dichlorobis (triphenylphosphine)palladium (II), 3.9 g of 3-(4-n-heptylphenyl)-5-(tributyltin)isoxazole obtained in (c), 2.4 g of 4-n-octyliodobenzene, and 50 ml of tetrahydrofuran was refluxed with stirring for 12 hours in an atmosphere of argon.

The reaction solution was poured into water, and an organic layer was extracted with ether. The ether layer was washed with water, and the resultant solution was dried with $Na_2SO_4$. Thereafter, the solvent was distilled off. The residue was purified by silica gel column chromatography using a mixed solvent of hexane-toluene (4 to 10:1) as an eluent and recrystallized with acetone to obtain 3-(4-n-heptylphenyl)-5-(4-n-octylphenyl)isoxazole (yield 0.58 g).

The purity of the compound thus obtained was 98.7% by HPLC (1 spot by TLC). Furthermore, from the relationship between the fact that a molecule ion peak was recognized at 431 by the result of an IR measurement and a MASS analysis and the materials used for synthesis, it was confirmed that the compound thus obtained was a title compound.

The liquid crystal compound of Example 1 was observed for phase changes under a polarizing microscope using Hot Stage FP-82 manufactured by Mettler Instrumente AG. The results are shown in the following Table 1.

TABLE 1

| | Phase transition temperature (° C.) | | | | | |
|---|---|---|---|---|---|---|
| | C | C' | $S_c$ | $S_A$ | Ne | I |
| Example 1 | • 54 | • 73.8 | • 89.2 | • 116 | | • |
| Example 2 | • 63 | • 76.4 | | • 102.2 | • 115.4 | • |
| Example 3 | • 53 | • 76.7 | • 125 | • 139.5 | • 140.5 | • |
| Example 4 | • 62 | | • 120.8 | • 125.7 | • 126.1 | • |
| Example 5 | • 69 | • 83.1 | • 95.7 | • 114.8 | | • |

The liquid crystal compound of Example 1 showed a negative $\Delta\epsilon$ (i.e., $\Delta\epsilon=-4.8$) which was measured at 10 KHz and 85° C. (at which the compound shows a smectic C phase).

This dielectric anisotropy was obtained as follows: the liquid crystal compound was injected into a homeotropically aligned cell with a thickness of 2.0 μm manufactured by EHC, and a dielectric constant εh in a molecule long axis direction was measured by using an LCR meter; on the other hand, the liquid crystal compound was injected into a horizontally aligned cell with a thickness of 5.0 μm manufactured by EHC, and a dielectric constant εp in a molecule short axis direction was similarly measured. From these values, the dielectric anisotropy $\Delta\epsilon=\epsilon h-\epsilon p$ was obtained.

EXAMPLE 2

In Example 2, 3-(4-n-heptylphenyl)-5-(4-n-pentylphenyl) isoxazole represented by the following Formula was synthesized.

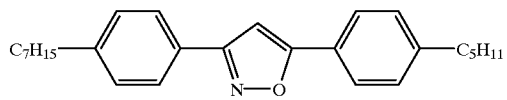

3-(4-n-heptylphenyl)-5-(4-n-pentylphenyl)isoxazole was obtained (yield 0.3 g) in the same way as in (d) of Example 1 except that 2.0 g of 4-n-pentyliodobenzene was used in place of 2.4 g of 4-n-octyliodobenzene.

The purity of the compound thus obtained was 99.0% by HPLC (1 spot by TLC). Furthermore, from the relationship between the fact that a molecule ion peak was recognized at 389 by the result of an IR measurement and a MASS analysis and the materials used for synthesis, it was confirmed that the compound thus obtained was a title compound.

The liquid crystal compound of Example 2 was observed for phase changes under a polarizing microscope using Hot Stage FP-82 manufactured by Mettler Instrumente AG. The results are also shown in Table 1.

EXAMPLE 3

In Example 3, 3-(4-n-heptylphenyl)-5-(4-n-octyloxyphenyl)isoxazole represented by the following Formula was synthesized.

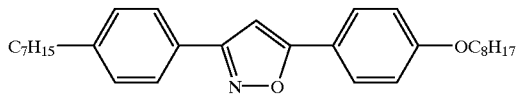

3-(4-n-heptylphenyl)-5-(4-n-octyloxyphenyl)isoxazole was obtained (yield 0.58 g) in the same way as in (d) of Example 1 except that 2.09 g of 4-n-octyloxybromobenzene and 50 ml of dioxane were used in place of 2.4 g of 4-n-octyliodobenzene and 50 ml of tetrahydrofuran.

The purity of the compound thus obtained was 98.9% by HPLC (1 spot by TLC). Furthermore, from the relationship between the fact that a molecule ion peak was recognized at 447 by the result of an IR measurement and a MASS analysis and the materials used for synthesis, it was confirmed that the compound thus obtained was a title compound.

The liquid crystal compound of Example 3 was observed for phase changes under a polarizing microscope using Hot Stage FP-82 manufactured by Mettler Instrumente AG. The results are also shown in Table 1.

EXAMPLE 4

In Example 4, 3-(4-n-heptylphenyl)-5-(3-fluoro-4-n-octyloxyphenyl)isoxazole represented by the following Formula was synthesized.

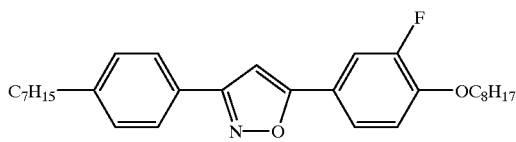

3-(4-n-heptylphenyl)-5-(3-fluoro-4-n-octyloxyphenyl) isoxazole was obtained (yield 0.71 g) in the same way as in (d) of Example 1 except that 2.22 g of 3-fluoro-4-n-octyloxybromobenzene and 50 ml of dioxane were used in place of 2.4 g of 4-n-octyliodobenzene and 50 ml of tetrahydrofuran.

The purity of the compound thus obtained was 98.9% by HPLC (1 spot by TLC). Furthermore, from the relationship between the fact that a molecule ion peak was recognized at 465 by the result of an IR measurement and a MASS analysis and the materials used for synthesis, it was confirmed that the compound thus obtained was a title compound.

The liquid crystal compound of Example 4 was observed for phase changes under a polarizing microscope using Hot Stage FP-82 manufactured by Mettler Instrumente AG. The results are also shown in Table 1. The liquid crystal compound of Example 4 in which $X_4$ is a fluorine atom exhibited a liquid crystal phase in a range of 62° C. to 126.1° C., whereas the liquid crystal compound of Example 3 in which $X_1$ to $X_4$ are hydrogen atoms exhibited a liquid crystal phase in a range of 76.7° C. to 140.5° C. Thus, the compound of Example 4 exhibited a liquid crystal phase at lower temperatures than those of the compound of Example 3.

EXAMPLE 5

In Example 5, 3,5-bis(4-n-octylphenyl)isoxazole represented by the following Formula was synthesized.

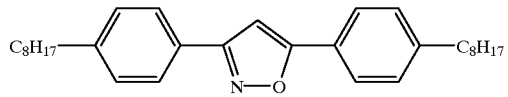

(a) Synthesis of 1,3-bis(4-n-octylphenyl)propane-1,3-dione

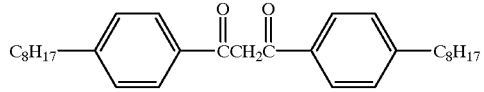

A solution containing 10 g of ethyl-4-n-octylbenzoate, 8.9 g of 4-n-octylacetophenone, and 40 ml of dimethoxyethane was dropped onto a suspension containing 3.5g of 60% sodium hydride and 70 ml of dimethoxyethane in an atmosphere of argon; and thereafter, the reaction solution was refluxed with stirring for 2 hours, and stirred overnight at room temperature.

The reaction solution was poured into water, and the resultant solution was acidified with 3N hydrochloric acid. Thereafter, an organic layer was extracted with ether. The ether layer was washed with saturated saline, and the resultant solution was dried with $Na_2SO_4$. The solvent was then distilled off. The residue was purified by silica gel column chromatography using a mixed solvent of hexane-toluene (2:1) as an eluent and recrystallized with ethanol to obtain 1,3-bis(4-n-octylphenyl)propane-1,3-dione (yield 10.4 g; GC 97.7%; Mass448 (M+)).

(b) Synthesis of 3,5-bis(4-n-octylphenyl)isoxazole

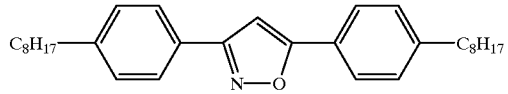

Five drops of 50% sodium hydroxide aqueous solution was added to a solution containing 6.1 g of 1,3-bis(4-n-octylphenyl)propane-1,3-dione obtained in (a), 1.84 g of hydroxylamine hydrochloride, and 200 ml of ethanol. The solution was refluxed with stirring for 2 hours.

Toluene was added to the reaction solution, and a separated organic layer was washed with saturated brine. The resultant solution was dried with $Na_2SO_4$, and the solvent was distilled off. The residue was recrystallized with acetone to obtain 3,5-bis(4-n-octylphenyl)isoxazole (yield 3.89 g).

The purity of the compound thus obtained was 99.4% by HPLC (1 spot by TLC). Furthermore, from the relationship between the fact that a molecule ion peak was recognized at 445 by the result of an IR measurement and a MASS analysis and the materials used for synthesis, it was confirmed that the compound thus obtained was a title compound.

The liquid crystal compound of Example 5 was observed for phase changes under a polarizing microscope using Hot Stage FP-82 manufactured by Mettler Instrumente AG. The results are shown in Table 1. In the liquid crystal compound of Example 5, $R_1$ and $R_2$ are both alkyl groups, and the compound exhibited a liquid crystal phase at a temperature in a range of 83.1° C. to 114.8C. In contrast, the liquid crystal compound of Example 3 in which $R_1$ is an alkyl group and $R_2$ is an alkoxy group exhibited a liquid crystal phase at a temperature in a wider range of 76.7° C. to 140.5° C.

Next, in Examples 6 and 7, the liquid crystal composition of the present invention containing the liquid crystal compound of the present invention and the liquid crystal display device of the present invention using the composition will be described.

Various measurements were conducted by the following methods.

A phase transition temperature was obtained by placing a sample on a slide glass covered with a cover glass on a hot plate and observing the sample under a polarizing microscope.

Figure 6:
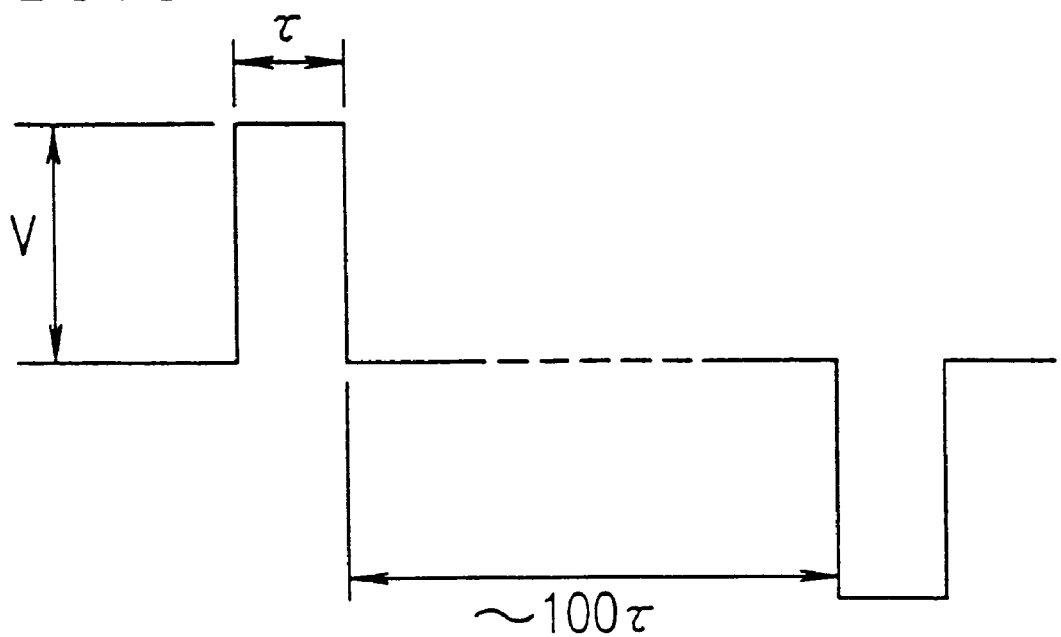
FIG. 6 is a waveform diagram showing a waveform of a pulse voltage applied to the liquid crystal display device in one embodiment of the present invention.

A voltage (V)-memory pulse width (τ) characteristic (τ–V characteristic) was measured by alternately applying two positive and negative monopolar pulses as shown in FIG. 6 to a liquid crystal display device without applying a bias voltage thereto, and observing a switching state under a polarizing microscope. A pulse interval was prescribed to be 100τ, which is 100 times the pulse width (τ) (see Ferroelectrics, 122 (1991) p. 63). Then, a voltage (V) of a monopolar pulse was changed, and a pulse width (τ) at which a 100% switching state was measured at each voltage, thereby obtaining a τ–V curve. From this τ–V curve, a voltage ($V_{min}$) and a pulse width (τ) at a local minimum value was obtained.

EXAMPLE 6

The liquid crystal compound of Example 1 was added to commercially available ferroelectric liquid crystal composition, SCE-8 (produced by Merck KGaA) in a proportion shown in Table 2 to obtain ferroelectric liquid crystal compositions A and B.

TABLE 2

|  | Example 6 | | Comparative Example 1 SCE-8 |
|---|---|---|---|
|  | Ferroelectric liquid crystal composition A | Ferroelectric liquid crystal composition B | |
| Liquid crystal compound of Example 1 | 10.0 wt % | 20.0 wt % | — |
| Optically active material | — | — | — |
| SCE-8 | 90.0 wt % | 80.0 wt % | 100.0 wt % |

Each of the ferroelectric liquid crystal compositions A and B was injected into a liquid crystal cell (thickness of ITO film 200 nm; no insulating film; thickness of polyimide alignment film 20 nm; parallel rubbing; cell thickness 2.0 μm) manufactured by EHC to produce a liquid crystal display device.

COMPARATIVE EXAMPLE 1

Commercially available ferroelectric liquid crystal composition, SCE-8 (produced by Merck KGaA) was injected into a liquid crystal cell (ITO film thickness 200 nm; no insulating film; thickness of polyimide alignment film 20 nm; parallel rubbing; cell thickness 2.0 μm) manufactured by EHC used in Example 6 to produce a liquid crystal display device.

Figure 7:
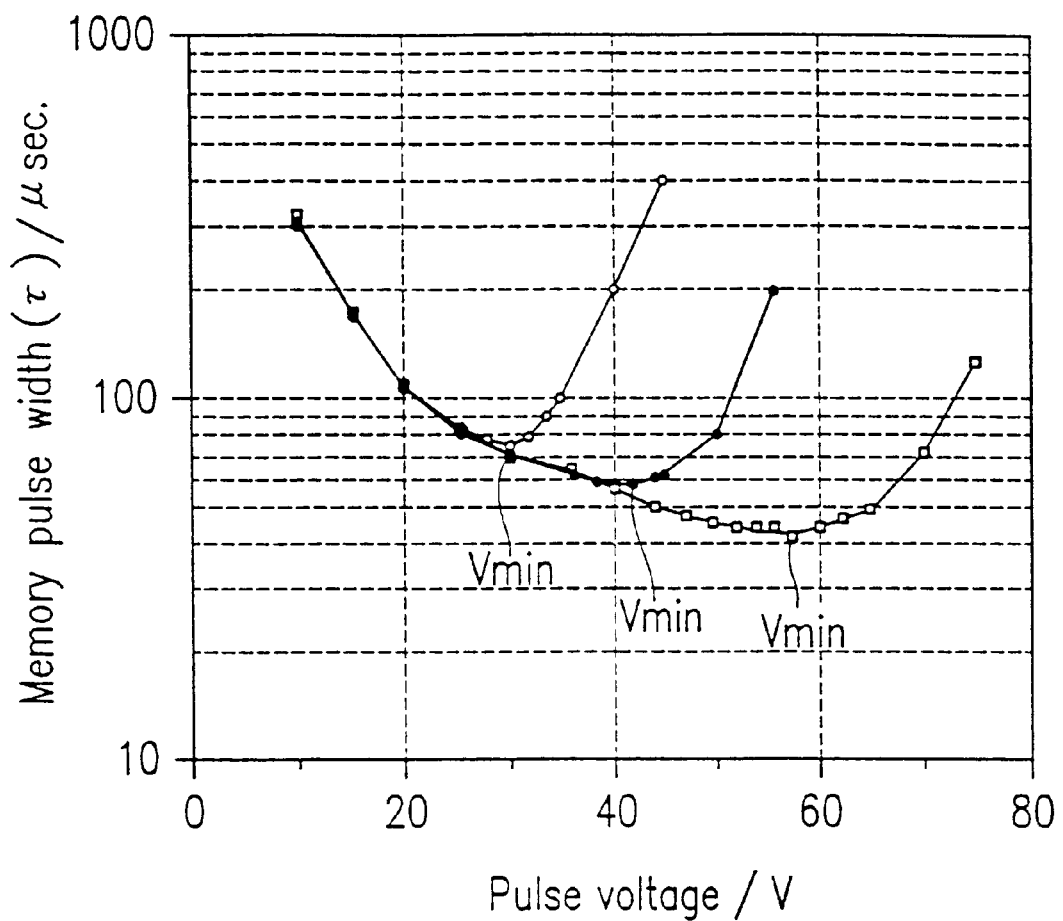
FIG. 7 is a graph showing voltage-memory pulse width characteristics of liquid crystal display devices in Example 6 and Comparative Example 1.

The τ–V characteristics of the liquid crystal display devices of Example 6 and Comparative Example 1 are as shown in FIG. 7. In this figure, ● represents the liquid crystal display device of Example 6 using the ferroelectric liquid crystal composition A, ○ represents the liquid crystal display device of Example 6 using the ferroelectric liquid crystal composition B, and □ represents the liquid crystal display device of Comparative Example 1 using SCE-8. It is understood from this figure that adding the liquid crystal compound of the present invention decreases a voltage $V_{min}$ at a local minimum value $\tau_{min}$ of a memory pulse width in accordance with the added amount. In the τ–V characteristics, the liquid crystal display device of Comparative Example 1 using SCE-8 and the liquid crystal display devices of Example 6 using the ferroelectric liquid crystal compositions A and B have the same characteristics at a voltage of 30 volts or less. This is because these ferroelectric liquid crystal compositions have identical spontaneous polarization $P_s$. On the other hand, adding the liquid crystal compound of the present invention decreases $V_{min}$, and the characteristics at a voltage higher than $V_{min}$ are changed. This is because the liquid crystal composition has a negative Δε with a larger absolute value as a result of the addition of the liquid crystal compound of the present invention. This agrees with the following relationship described in the prior art between $V_{min}$, and spontaneous polarization $P_s$ and dielectric anisotropy Δε.

$$V_{min} = P_s \cdot d / \left( \sqrt{3} \cdot \varepsilon_o \cdot \Delta \varepsilon \cdot \sin^2 \theta \right)$$

EXAMPLE 7

A mixture of an optically active compound represented by the following Formula was added to commercially available ferroelectric liquid crystal composition, SCE-8 (produced by Merck KGaA) in an amount of 0.5% by weight to obtain a ferroelectric liquid crystal composition C shown in the following Table 3.

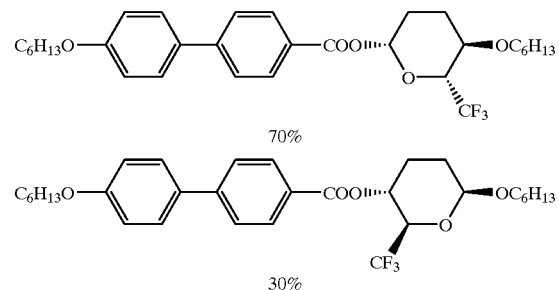

TABLE 3

|  | Example 7 | | Comparative Example 2 SCE-8 |
|---|---|---|---|
|  | Ferroelectric liquid crystal composition D | Ferroelectric liquid crystal composition E | Ferroelectric liquid crystal composition C |
| Liquid crystal compound of Example 1 | 5.0 wt % | 10.0 wt % | — |
| Optically active material | 0.5 wt % | 0.5 wt % | 0.5 wt % |
| SCE-8 | 94.5 wt % | 89.5 wt % | 99.5 wt % |

The liquid crystal compound of Example 1 was added to the ferroelectric liquid crystal composition C in a proportion shown in Table 3 to obtain ferroelectric liquid crystal compositions D and E.

A liquid crystal cell was produced as follows. transparent electrodes made of ITO with a thickness of 200 nm were formed on two glass substrates, respectively. An insulating film made of SiO₂ with a thickness of 50 nm was formed on the transparent electrodes, and an alignment film made of polyimide with a thickness of 50 nm was coated onto the insulating film, followed by rubbing. These two glass substrates were placed so as to oppose each other in such a manner that the rubbing directions became parallel to each other. Then, the substrates were attached to each other so as to have a cell gap of 1.5 μm.

The ferroelectric liquid crystal compositions D and E are respectively injected into the liquid crystal cell. Thereafter, each of the cells was once heated to a temperature at which the ferroelectric liquid crystal composition changes to isotropic liquid. Then, each cell was gradually cooled to room temperature, whereby liquid crystal display devices having a C2 alignment in the entire pixels were obtained.

COMPARATIVE EXAMPLE 2

The ferroelectric liquid crystal composition C obtained in Example 7 was injected into the liquid crystal cell produced in Example 7, thereby producing a liquid crystal display device.

Figure 8:
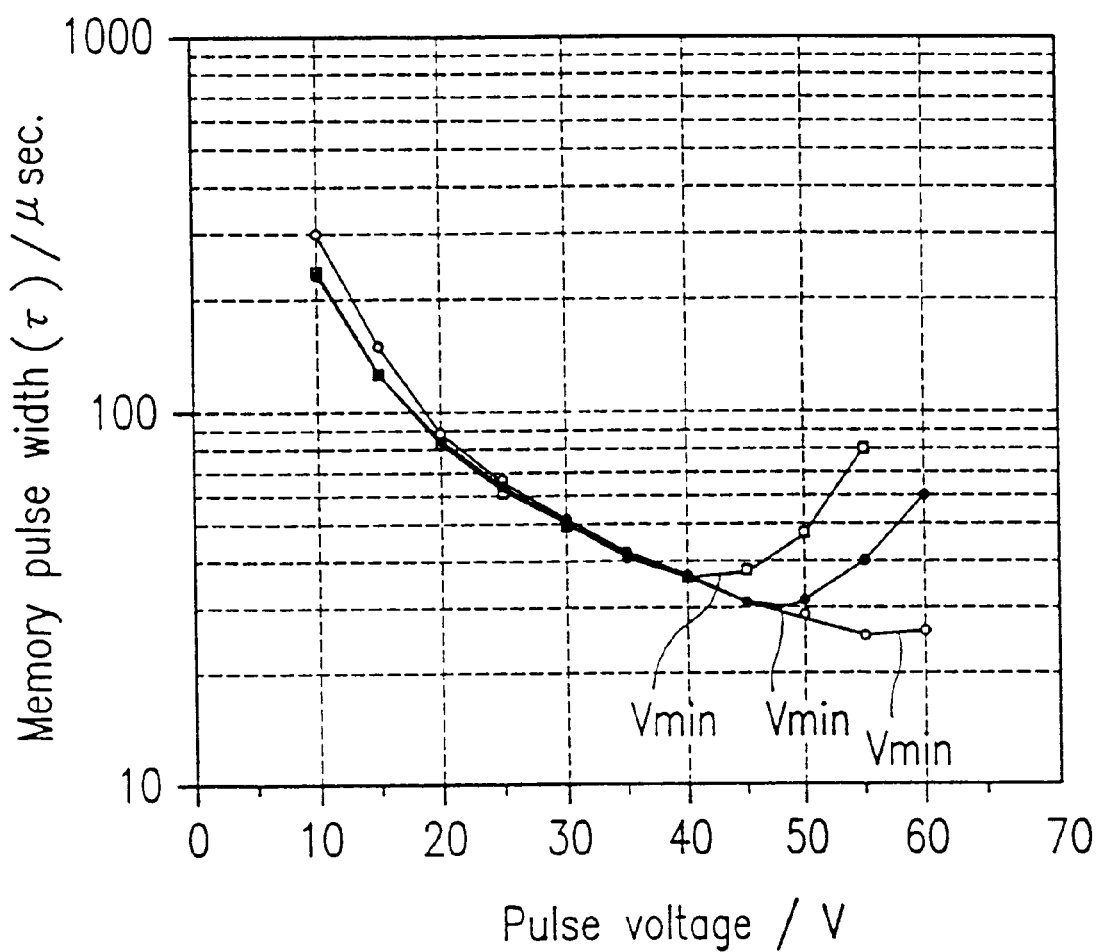
FIG. 8 is a graph showing voltage-memory pulse width characteristics of liquid crystal display devices in Example 7 and Comparative Example 2.
Figure 9:
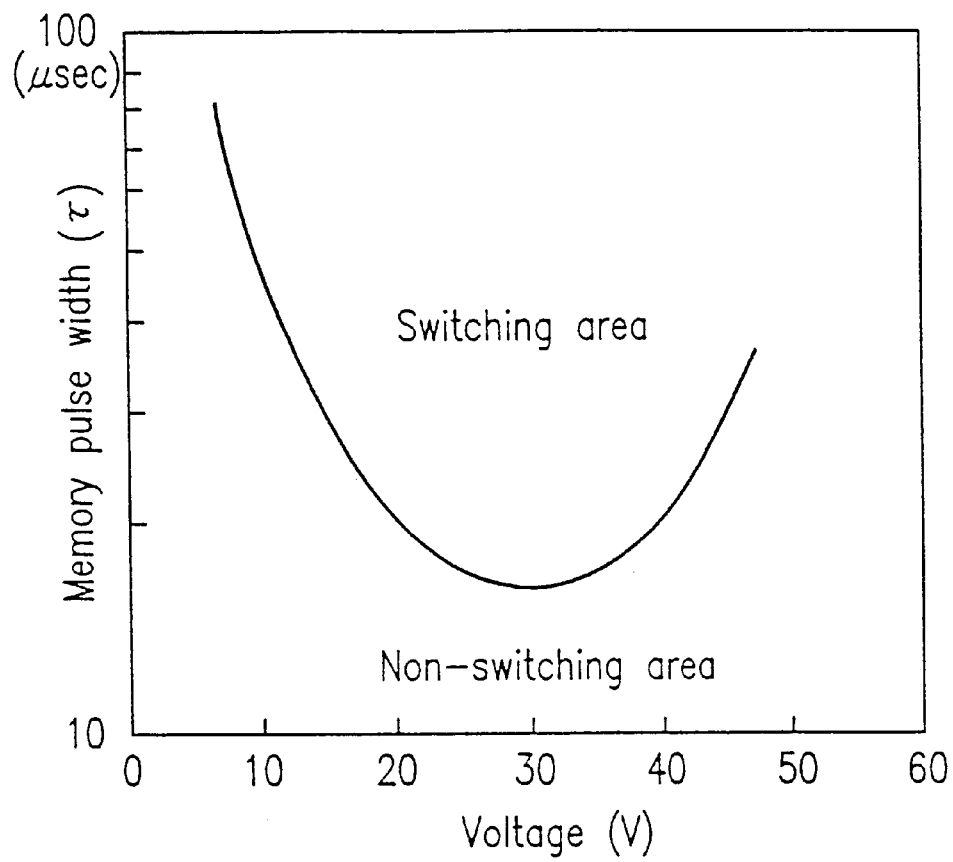
FIG. 9 is a graph showing a voltage-memory pulse width characteristic of a ferroelectric liquid crystal composition having a negative Δε.
Figure 10:
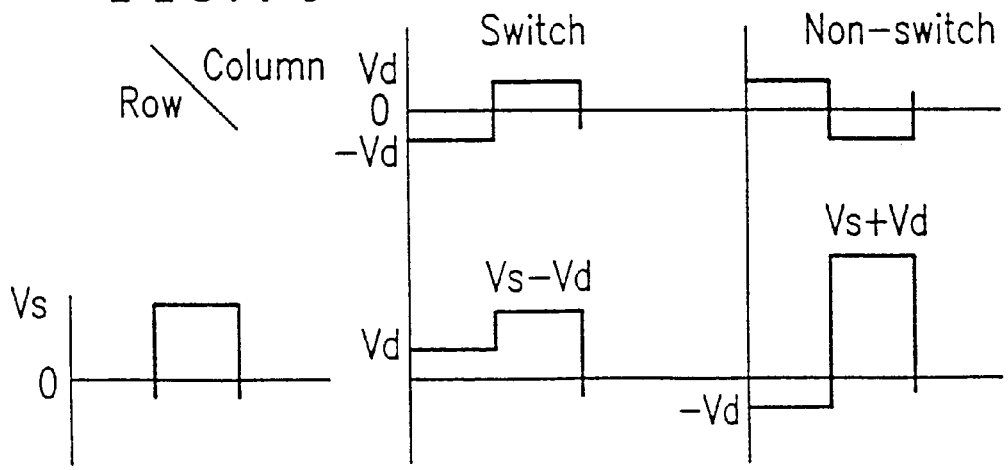
FIG. 10 is a waveform diagram showing waveforms of a pulse voltage applied when an operation characteristic shown in FIG. 9 is measured.

The τ-V characteristics of the liquid crystal display devices of Example 7 and Comparative Example 2 are as shown in FIG. 8. In this figure, ● represents the liquid crystal display device of Example 7 using the ferroelectric liquid crystal composition D, □ represents the liquid crystal display device of Example 7 using the ferroelectric liquid crystal composition E, and ○ represents the liquid crystal display device of Comparative Example 2 using the ferroelectric liquid crystal composition C. It is understood from this figure that adding the liquid crystal compound of the present invention decreases a voltage $V_{min}$ at a local minimum value $τ_{min}$ of a memory pulse width in accordance with the added amount. Regarding the τ-V characteristics, in the liquid crystal display device of Comparative Example 2 using the ferroelectric liquid crystal composition C, $V_{min}$ was high enough to exceed 50 volts. However, in the ferroelectric liquid crystal composition D with the liquid crystal compound of the present invention added, $V_{min}$ was decreased to 47 volts, and in the ferroelectric liquid crystal composition E with the liquid crystal compound of the present invention added, $V_{min}$ was decreased to 42 volts.

As described above, according to the present invention, a liquid crystal compound having a negative Δε with a large absolute value and a low viscosity can be obtained. Thus, $V_{min}$ can be decreased in the τ-$V_{min}$ driving method of a liquid crystal display device, and the liquid crystal display device can be driven at a high speed by using the liquid crystal compound of the present invention. Furthermore, in the liquid crystal display device, a stable memory property can be obtained by utilizing the AC stabilizing effect. Therefore, a liquid crystal display device with a high contrast, an outstanding display quality, a simple structure, and a low power consumption can be provided.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A liquid crystal compound represented by the following general formula I:

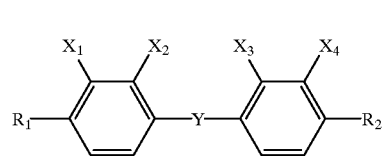

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

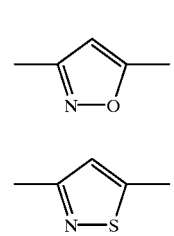

2. A liquid crystal compound according to claim 1, wherein —Y— in the general Formula (I) is a group represented by the Formula (II).

3. A liquid crystal compound according to claim 1, having a negative dielectric anisotropy Δε.

4. A liquid crystal composition comprising at least one kind of liquid crystal compound represented by the following general Formula (I):

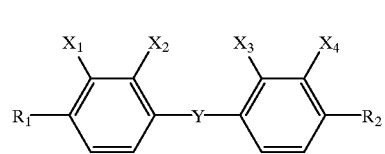

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

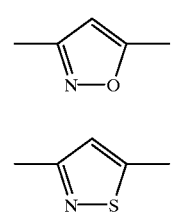

5. A liquid crystal composition according to claim 4, having a negative dielectric anisotropy Δε.

6. A liquid crystal composition according to claim 4, having a phase series exhibiting isotropic liquid, a nematic phase, a smectic A phase, and a smectic C phase in a decreasing order of temperature.

7. A liquid crystal composition according to claim 6, having ferroelectricity.

8. A liquid crystal composition according to claim 7, further comprising at least one kind of optically active compound.

9. A liquid crystal display device, comprising a pair of substrates opposing each other and a liquid crystal layer provided between the substrates, the liquid crystal layer containing a ferroelectric liquid crystal composition containing at least one kind of liquid crystal compound represented by the following general Formula (I):

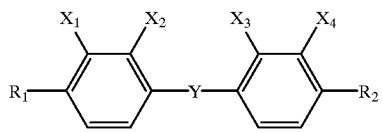
(I)

wherein $R_1$ and $R_2$ are independently a linear or branched alkyl group or alkoxy group having 1 to 14 carbon atoms, provided that at least one of $R_1$ and $R_2$ is an alkyl group; —Y— is a group represented by the following Formula (II) or (III); and $X_1$, $X_2$, $X_3$, and $X_4$ are independently a hydrogen atom or a fluorine atom:

(II)

-continued (III)

10. A liquid crystal display device according to claim 9, wherein the liquid crystal layer has an identical pretilt angle at an interface between the liquid crystal layer and one of the pair of substrates with a pretilt angle at an interface between the liquid crystal layer and the other of the pair of substrates, and has a chevron layer structure, wherein a bending direction of the chevron layer structure is identical with a direction of the pretilt angle.

11. A liquid crystal display device according to claim 9, wherein the ferroelectric liquid crystal composition has a negative dielectric anisotropy $\Delta\epsilon$ and a local minimum value in a voltage-memory pulse width characteristic.

12. A liquid crystal display device according to claim 10, wherein the pretilt angle is in a range of 1° to 15°.

13. A liquid crystal compound according to claim 1, wherein $R_1$ and $R_2$ are each independently selected from the group consisting of pentyl, heptyl, octyl and octyloxy.

14. A liquid crystal composition according to claim 4, wherein $R_1$ and $R_2$ are each independently selected from the group consisting of pentyl, heptyl, octyl and octyloxy.

15. A liquid crystal display device according to claim 9, wherein $R_1$ and $R_2$ are each independently selected from the group consisting of pentyl, heptyl, octyl and octyloxy.

* * * * *